United States Patent
Lubitz et al.

(10) Patent No.: US 10,526,574 B2
(45) Date of Patent: Jan. 7, 2020

(54) FED-BATCH PROCESS FOR THE PRODUCTION OF BACTERIAL GHOSTS

(71) Applicant: BIRD-C GMBH & CO KG, Vienna (AT)

(72) Inventors: Werner Lubitz, Kritzendorf (AT); Christian Herwig, Vienna (AT); Timo Langemann, Kritzendorf (AT); Patrick Sagmeister, Vienna (AT)

(73) Assignee: Bird-C GmbH & Co. KG, Kritzendorf (AT)

(*) Notice: Subject to any disclaimer, the term of this patent is extended or adjusted under 35 U.S.C. 154(b) by 580 days.

(21) Appl. No.: 15/120,327

(22) PCT Filed: Feb. 20, 2015

(86) PCT No.: PCT/EP2015/053599
§ 371 (c)(1),
(2) Date: Aug. 19, 2016

(87) PCT Pub. No.: WO2015/124717
PCT Pub. Date: Aug. 27, 2015

(65) Prior Publication Data
US 2018/0201895 A1 Jul. 19, 2018

Related U.S. Application Data

(60) Provisional application No. 61/942,695, filed on Feb. 21, 2014.

(51) Int. Cl.
*C12N 1/06* (2006.01)
*C12N 1/20* (2006.01)
*C07K 14/005* (2006.01)

(52) U.S. Cl.
CPC .............. *C12N 1/06* (2013.01); *C07K 14/005* (2013.01); *C12N 1/20* (2013.01); *C12N 2795/14211* (2013.01); *C12N 2795/14222* (2013.01)

(58) Field of Classification Search
None
See application file for complete search history.

(56) References Cited

U.S. PATENT DOCUMENTS
2012/0040829 A1  2/2012  Lubitz et al.

FOREIGN PATENT DOCUMENTS
WO  2009/090093 A1  7/2009

OTHER PUBLICATIONS

Carvell et al., Cytotechnology 50:35-48 (Year: 2006).*
Yee et al., Biotech. Bioeng., 41: 781-790 (Year: 1993).*
Huter V et al: "Bacterial ghosts as drug carrier and targeting vehicles", Journal of Controlled Release, Elsevier, Amsterdam, NL, vol. 61, No. 1-2, Aug. 27, 1999 (Aug. 27, 1999), pp. 51-63, XP004362963, ISSN: 0168-3659, DOI: 10.1016/S0168-3659(99)00099-1 section 3.2.
(Continued)

*Primary Examiner* — Nancy A Treptow
(74) *Attorney, Agent, or Firm* — Rothwell, Figg, Ernst & Manbeck, P.C.

(57) ABSTRACT

The invention relates to a fed-batch process for the production of bacterial ghosts based on the decoupling of the lytic gene expression and actual lysis of bacterial cells.

31 Claims, 6 Drawing Sheets

(56) References Cited

OTHER PUBLICATIONS

Figure 1:
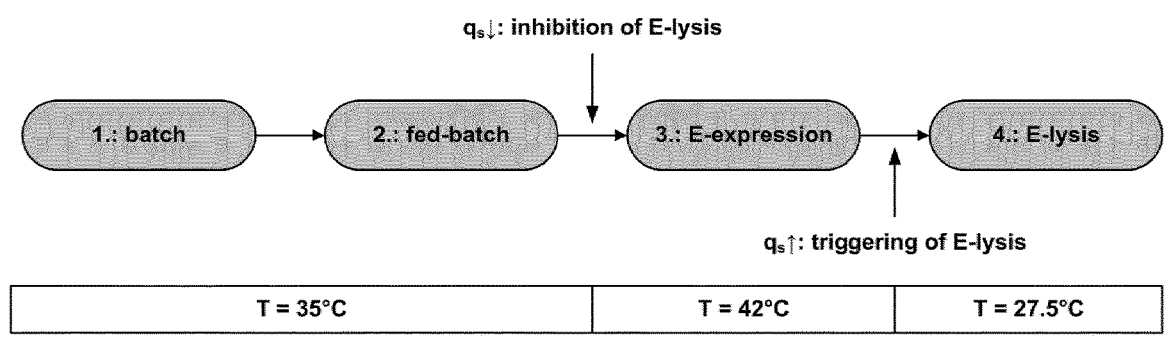

Timo Langemann et al: "The Bacterial Ghost platform system: production and applications", Bioengineered Bugs, Landes Bioscience, US, vol. 1, No. 5, Sep. 1, 2010 (Sep. 1, 2010), pp. 326-336, XP002672825, ISSN: 1949-1018, DOI: 10.4161/BBUG.1.5.12540 Whole doc, in particular p. 326, col. 2, 1.18-23.

Lubitz W et al: "Lysis of *Escherichia coli* after infection with [phi]X174 depends on the regulation of the cellular autolytic system", Journal of General Microbiology 1984 GB, vol. 130, No. 5, 1984, pp. 1079-1087, XP002738781, ISSN: 0022-1287 Results (p. 1081-1082, 1085), discussion.

Marchart J et al: "Pasteurella multocida-and Pasteurella haemolytica-ghosts: new vaccine candidates", Vaccine, Elsevier LTD, GB, vol. 21, No. 25-26, Sep. 8, 2003 (Sep. 8, 2003), pp. 3988-3997, XP004446176, ISSN: 0264-410X, DOI: 10.1016/S0264-410X(03)00383-9 Section 3.2, Fig.1.

Hoffelner H et al: "Recombinant bacterial ghosts: versatile targeting vehicles and promising vaccine candidates", International Journal of Medical Microbiology, Urban Und Fischer, DE, vol. 294, No. 5, Oct. 15, 2004 (Oct. 15, 2004), pp. 303-311, XP004960103, ISSN: 1438-4221, DOI: 101016/J.IJMM.2004.04.003 Whole doc., in particular p. 304, col. 2.

International Search Report cited in PCT/EP2015/053599 dated May 12, 2015, 3 pages.

\* cited by examiner (A)　　　　　　　　　　　　　　　　(B)

FED-BATCH PROCESS FOR THE PRODUCTION OF BACTERIAL GHOSTS

CROSS REFERENCE TO RELATED APPLICATION

This application is a 35 U.S.C. 371 National Phase Entry Application from PCT/EP2015/053599, filed Feb. 20, 2015, which claims the benefit of U.S. Provisional Patent Application No. 61/942,695 filed on Feb. 21, 2014, the disclosures of which are incorporated herein in their entirety by reference.

The invention relates to a fed-batch process for the production of bacterial ghosts based on the decoupling of the lytic gene expression and actual lysis of bacterial cells.

The bacterial ghost platform system is a promising new technology for medicinal applications. Derived from Gram-negative bacteria, bacterial ghosts are empty bacterial cell envelopes with sustained cellular morphology. Bacterial ghosts are produced from viable bacteria by controlled heterologous expression of a lytic gene, for example, the bacteriophage φX174 lytic gene E. The encoded protein E is a short (91 aa) non-enzymatic membrane associated protein that targets cell division sites where it oligomerizes and induces fusion of the inner and outer membrane (Witte et al., 1990. J. Bacteriol., 172(7): 4109-4114). This eventually results in the formation of a distinct trans-membrane tunnel structure sealing the periplasmic space. Driven by the osmotic pressure difference between the cytoplasm and the surrounding medium, the cytoplasm with all its constituents is expelled to the medium leaving behind an empty bacterial ghost.

The use of bacterial ghosts as dead vaccines or adjuvants and the preparation of recombinant bacterial ghosts carrying heterologous proteins in their cell envelope structures is disclosed in WO 91/13555 and WO 93/01791, herein incorporated by reference. Bacterial ghosts are further suitable as carriers or targeting vehicles for active compounds as described in WO 00/53163, herein incorporated by reference.

The broad spectrum of bacterial ghosts applications urge for an economic, robust and scalable procedure for their manufacture.

Conventional bacterial ghost production approaches are carried out in batch mode. A low density batch process in complex medium has been described in Langemann et al., 2010 Bioengineered bugs, 1(5): 326-336. Current production of *Escherichia coli* bacterial ghosts is realized with a medium density batch process in defined medium adapted from DeLisa et al., 1999 Biotechnol. Bioeng., 65(1): 54-64. In this process (biomass dry cell weight (DCW) of about 5 g/l before lysis induction), a final concentration of $10^{10}$ cells/ml culture broth can be reached. The E-lysis efficiency exceeds 99.8%.

It would be desirable to provide a more efficient method for producing bacterial ghost using a high density batch process approach. Previous approaches of this type however have proven problematic. At high cell densities, the expulsion of large amounts of cytoplasmic content into the medium drastically changes the characteristics of the culture broth. This results in serious problems such as increased viscosity, foaming, reduced oxygen transfer and bad mass transfer.

It is an object of the present invention to provide a method for producing bacterial ghost preparation, wherein the disadvantages of previous approaches have been overcome. This object is achieved by using a high-cell density cultivation method based on the decoupling of the lytic gene expression and the actual cell lysis process resulting in a high overall lysis efficiency.

Thus, a first aspect of the present invention relates to a method for producing a bacterial ghost preparation comprising the following steps:

(a) providing bacterial cells comprising a lytic gene encoding a protein capable of forming a tunnel structure in the bacterial cell envelope, (b) cultivating the bacterial cells under conditions wherein the lytic gene is not expressed, (c) after step (b), subjecting the bacterial cells to conditions wherein the lytic gene is expressed but lysis of the bacterial cells is repressed, (d) after step (c), subjecting the bacterial cells to conditions wherein lysis of the bacterial cells takes place, and (e) obtaining the resulting bacterial ghosts.

The bacterial cells provided in step (a) may be from any type of bacteria suitable for bacterial ghost production, e.g. Gram-negative bacterial cells, particularly *Escherichia coli* (e.g. as described in EP-A-0 291 021 and EP-A-0 516 655, herein incorporated by reference), *Salmonella typhimurium*, *Salmonella enteritidis*, *Klebsiella pneumoniae*, *Bordetella bronchiseptica*, *Heliobacter pylori*, *Vibrio cholerae*, *Actinobacillus pleuropneumoniae*, *Haemophilus influenzae*, *Mannheimia haemolytica*, *Pasteurella multocida*, *Pseudomonas aeruginosa*, *Pseudomonas putida*, *Ralstonia eutropha* or *Pectobacterium cypripedii*.

The bacterial cells comprise a lytic gene encoding a protein capable of forming a tunnel structure in the bacterial envelope (lytic protein). This lytic gene may be any suitable type of lytic gene, e.g. gene E, preferably the bacteriophage ΦX174 lytic gene E (Henrich et al., 1982 Mol. Gen. Genet., 185(3) 493-497), including naturally occurring or recombinant variants thereof. The lytic gene is extra-chromosomal or is integrated into the genome of the bacterial cell.

In step (b), the bacterial cells are cultivated under conditions where the lytic gene is not expressed. For this purpose, the lytic gene is preferably placed under operative control of a regulatable promoter, e.g. a chemically or thermally regulatable promoter.

Different chemically regulatable promoter/operator systems may be used to control the expression of the lytic gene, including the lac promoter, trp promoter, tet promoter, tac promoter, trc promoter or derivatives thereof by adding a chemical compound capable of inducing the expression of a gene under operative control of a promoter. Examples of inducing chemical compounds are IPTG, isopropyl-D-thiogalactopyranoside, lactose or arabinose.

When the expression of the lytic gene is under operative control of a thermally regulatable promoter, a temperature-inducible lambda $P_R$ or $P_L$ promoter or derivatives thereof may be used, optionally in combination with a modified operator sequence and a temperature-sensitive cI857 repressor (e.g. as described in WO 98/07874, herein incorporated by reference), such as an $\lambda p_L/\lambda p_R$-cI857 system. A thermally regulatable promoter may be induced by adjusting the temperature to an expression permissive temperature. An expression permissive temperature is defined by the necessary temperature to reach to induce the expression of the lytic gene. In the present invention, it is preferred to use a thermally regulatable promoter which is repressed at a temperature of about 30° C.-37° C. and which can be induced by increasing the temperature to about 40-50° C., preferably about 42-45° C. for a period of, e.g. about at least 10 min.

In a preferred aspect of the invention, the cultivation of bacterial cells for the production of bacterial ghosts is carried out in a fed-batch process, i.e. in a cultivation process wherein one or more nutrients are supplied to a bioreactor during cultivation and wherein the cells remain in the bioreactor until the end of the cultivation.

In a further preferred aspect, the bacterial cells are cultivated in step (b) to a final biomass concentration of about 10-100 g DCW/L, preferably of about 20-80 g DCW/L, more preferably of about 30-70 g DCW/L, most preferably of about 40-60 g DCW/L culture medium.

In step (c), the bacterial cells are subjected to conditions wherein the lytic gene is expressed but lysis of bacterial cells is repressed. The lytic gene expression may be triggered by inducing the regulatable promoter as described above. To decouple lytic gene expression and protein lysis process, it has been found that the lysis process can be repressed when the bacterial cells are kept at an at least substantially stationary, e.g. a pseudo-stationary or a stationary state.

Alternatively, the lysis process can also be inhibited by pH values below 6 or above 8 (Lubitz et al., 1984 J. Gen. Microbiol., 130(5), 1079-1087).

In a preferred embodiment, the lysis of the bacterial cells is controlled by adjustment of the specific substrate uptake rate $q_S$.

The specific substrate uptake rate $q_S$ (amount of substrate consumed per time in g/gh) is defined by the ratio of the volumetric substrate uptake rate $r_S$ (amount of substrate consumed per time in g/lh) and the biomass concentration X (dry cell weight in g/l) according to Equation 1.

Equation 1

Definition of the specific substrate uptake rate in g/gh.

$$q_s = \frac{r_s}{X}$$

According to the present invention, the specific substrate rate $q_S$ was surprisingly identified as a critical parameter to control the lysis of the bacterial cells. The specific substrate rate $q_S$ is a quantifiable controllable process parameter impacting the cell physiology, especially during the lytic gene expression phase and subsequent lysis process. Therefore, the lytic functionality of the lytic protein is correlated with a lysis-competent physiological state of the bacterial cells, e.g. a physiological state allowing the bacterial cells to proceed to lysis. Thus, it is possible to express the lytic gene without lysing the cells by shifting the culture to a non-lysis-competent physiological state of the bacterial cells.

Thus, in step (b), the cultivation of the bacterial cells for the production of bacterial ghosts is preferably performed at a specific substrate uptake rate $q_S$ of at least about 0.4 g/gh, preferably at least about 0.5 g/gh, more preferably at least about 0.6 g/gh, most preferably at least about 0.7 g/gh. Subsequently, in step (c), an at least substantially stationary state may be obtained by shifting the cells to a state of low specific substrate uptake $q_S$, particularly wherein the specific substrate uptake rate $q_S$ is about 0.1-0.3 g/gh, more particularly 0.2-0.25 g/gh.

In step (d), the bacterial cells are subjected to conditions wherein lysis of the bacterial cells takes place. The onset of the lysis process can be triggered by resetting the culture to a lysis-competent physiological state of the bacterial cells, e.g. to a state wherein the specific substrate uptake $q_S$ is high. Thus, the lysis of the bacterial cells may be induced by providing a growth impulse, particularly by providing nutrients to the culture medium, more particularly by providing nutrients to the culture medium to obtain a substrate uptake rate $q_S$ of at least about 0.4 g/gh, preferably at least about 0.5 g/gh, more preferably at least about 0.6 g/gh, most preferably at least about 1.0 g/gh.

In a preferred embodiment, after subjecting the bacterial cells to lytic conditions, step (d) may comprise an additional promoter induction step, also called "polishing step", e.g. a chemically or a thermally promoter induction step can be carried out (see Example 7). This "polishing step" is preferably applied towards the end of the lysis process phase, e.g. without reducing the feed rate $q_S$.

The amount of residual non-lysed, reproductive bacterial cells within the ghost preparation may be further reduced by an inactivation step. This inactivation step may comprise adding a chemical inactivator capable of destroying the residual non-lysed bacterial cells, such as beta-propiolactone, as described in WO 2009/090093, herein incorporated by reference.

Alternatively, the inactivation of residual non-lysed bacterial cells can be achieved by co-expressing an enzyme capable of hydrolyzing cytoplasmic components, particularly a nuclease, more particularly a Staphylococcal nuclease (S-nuclease), as described in WO 2009/090093, herein incorporated by reference. The nuclease is encoded by a nuclease gene which is extra-chromosomal or already integrated into the genome of the bacterial cells. The expression of the nuclease gene may be in operative linkage with a regulatable expression control sequence (as described in WO 2009/090093).

A desirable goal for a bacterial ghosts preparation is to achieve a high lysis efficiency. The lysis efficiency is defined by the percentage of dead cells after the lysis step. According to the invention, a lysis efficiency of at least about 70%, preferably at least about 80%, more preferably at least about 90%, most preferably at least 96% is reached.

Further, the method of the invention may comprise controlling the culture conditions, e.g. by radio frequency impedance measurement (RFI) and/or soft-sensored-based biomass estimation which can be used in both regular and decoupled fed-batch processes for bacterial ghosts production. The culture medium conditions may be monitored at least during step (c) and step (d), particularly by radio frequency impedance measurement (see Example 2).

It has been found that the relative permittivity signal as measured by RFI reflects the accumulated capacitance of individual living cells (due to the existing membrane potential) which correlates linearly with the living cell count, allowing the observation of the lysis process in real-time. On the basis of the RFI signal, a strategy may be implemented providing control of the specific substrate uptake rate $q_S$ within the lysis phase (see Example 6). Using a sensor, e.g. a first principle soft-sensor, a calibration between relative permittivity and viable biomass can be carried out at-line without prior strain-specific information (see Example 3).

In another aspect, the present invention relates to the production of a protein of interest using the above described lysis strategy. By means of his method, large amounts of the protein of interest may be rapidly released into the culture medium and collected therefrom.

Thus, a method for recombinantly producing a protein of interest comprises the steps:

(a) providing bacterial cells comprising (i) a lytic gene encoding a protein capable of forming a tunnel structure in the bacterial cell envelope and (ii) a gene encoding a protein of interest, (b) cultivating the bacterial cells under conditions wherein the lytic gene is not expressed, (c) after step (b), subjecting the bacterial cells to conditions wherein the lytic gene is expressed but lysis of the bacterial cells is repressed, (d) after step (c), subjecting the bacterial cells to conditions wherein lysis of the bacterial cells takes place, and (e) recovering and optionally purifying the protein of interest, which has been expressed during step (b) and/or step (c).

The protein of interest can be any protein, e.g. an eukaryotic protein suitable for pharmaceutical purposes. It is encoded by a heterologous gene (gene of interest) which may be present in an extra-chromosomal form, e.g. encoded on an extra-chromosomal plasmid or integrated into the bacterial chromosome. Preferably, the gene of interest is under operative control of a regulatable promoter as described above. The promoter controlling the expression of the gene of interest may be the same or different as the promoter controlling the expression of the lytic gene. Preferably, the expression of the gene of interest is induced independently or from the expression of the lytic gene. For further preferred features of the method for producing a protein of interest, reference is made to the disclosure hereinabove to the discussions for producing bacterial ghosts.

In another aspect, the present invention relates to a method for recombinantly producing bacteriophage ΦX174 protein E or derivatives thereof comprising the steps:

(a) providing bacterial cells comprising a lytic gene encoding the protein E or derivatives thereof, (b) cultivating the bacterial cells under conditions wherein the lytic gene is not expressed, (c) after step (b), subjecting the bacterial cells to conditions wherein the lytic gene is expressed but lysis of the bacterial cells is repressed, (d) after step (c), subjecting the bacterial cells to conditions wherein lysis of the bacterial cells takes place, and (e) recovering and optionally purifying the protein E or derivatives thereof.

For preferred features of the method for producing bacteriophage ΦX174 protein E or derivatives thereof, reference is made to the disclosure hereinabove.

Further, the invention shall be explained in more detail by the followings figures and examples.

FIGURES

FIG. 1: Concept of the bacterial ghost production process with decoupled E-lysis. Schematic view of the process phases with indications of T and $q_S$ shows that decoupling of E-expression and E-lysis may be realized by controlling $q_S$. The process is divided in (1+2) a batch/fed-batch phase for accumulation of biomass, (3) an E-expression phase where protein E formation is induced by a temperature upshift at low $q_S$-values followed by (4) an E-lysis phase at lower temperatures with increased $q_S$-values.

Figure 2:
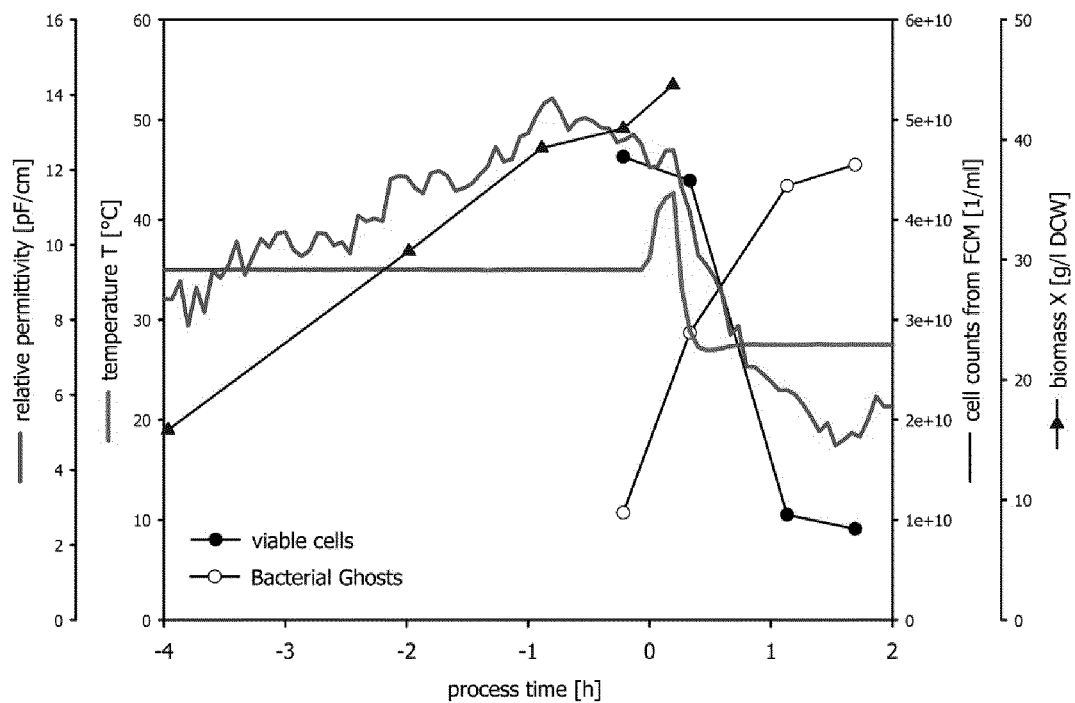

FIG. 2: Decoupling E-lysis by a simple temperature (red line) shift. During the temperature shift, both the relative permittivity (green line) and the cell viability (whole spheres line) remain largely unaffected. After a delay, the cell viability drops while at the same time bacterial ghosts are formed (empty spheres line).

Figure 3:
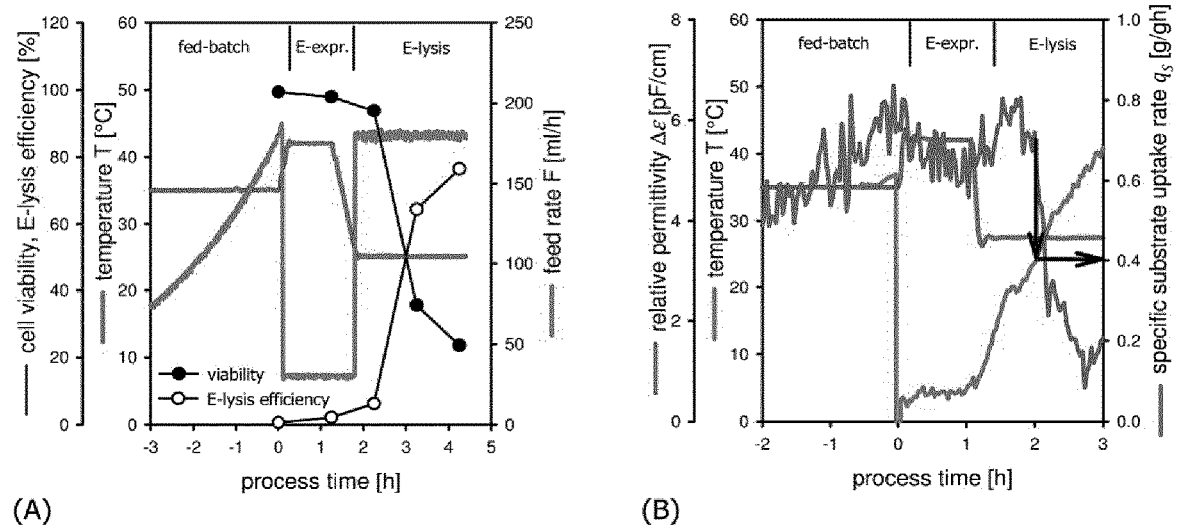

FIG. 3: (A) Demonstration of the decoupled E-lysis process in 2 l scale. The process phases are marked: fed-batch ($q_S$=0.6 g/gh, T=35° C.), E-expression ($q_S$=0.1 g/gh, T=42° C.) and E-lysis ($q_S$=0.6 g/gh, T=27.5° C.). The cell viability and the E-lysis efficiency as detected by Flow Cytometry Measurements (FCM) is indicated by whole and empty spheres, respectively. (B) Finding the minimal $q_S$ value which triggers the E-lysis at T=27.5° C.

Figure 4:
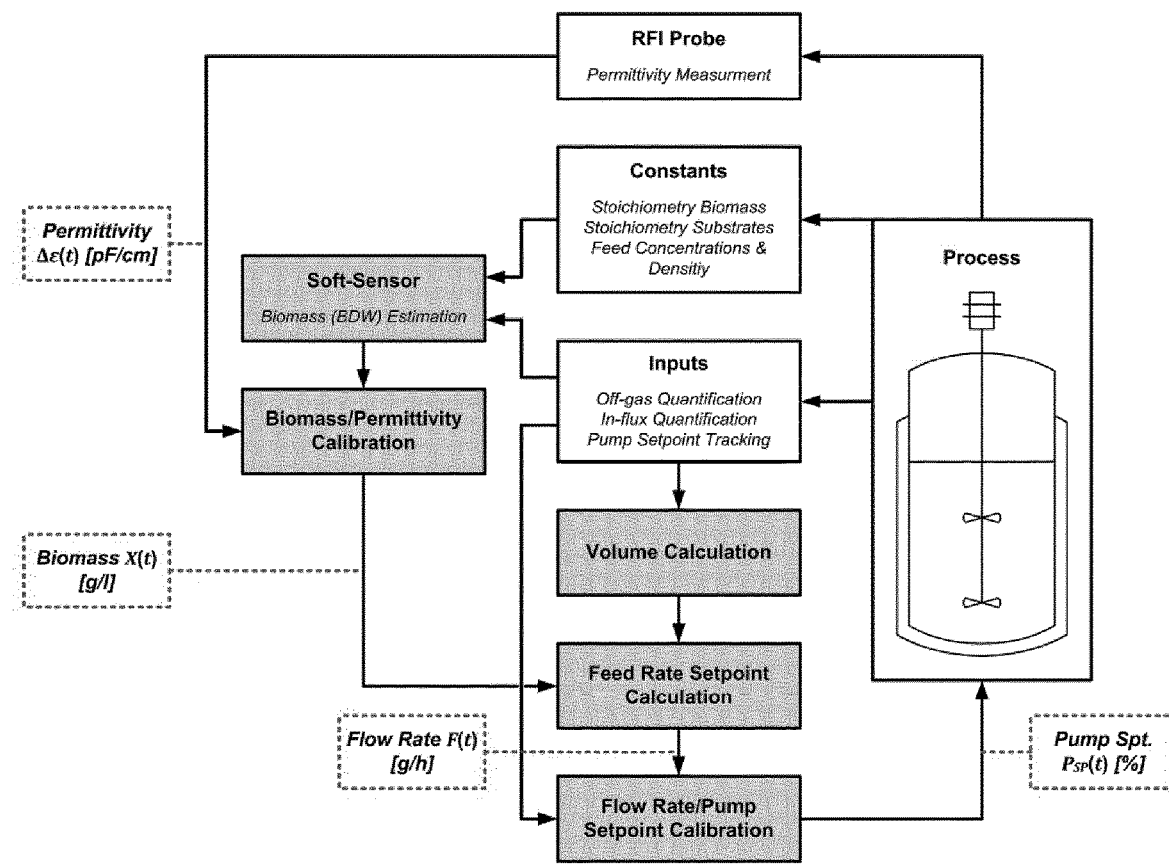

FIG. 4: Scheme of a strategy for controlling $q_S$ during the highly dynamic E-lysis phase. Computation/soft-sensing steps are shaded in grey. (Intermediate) outputs are given in boxes with dotted blue lines.

Figure 5:
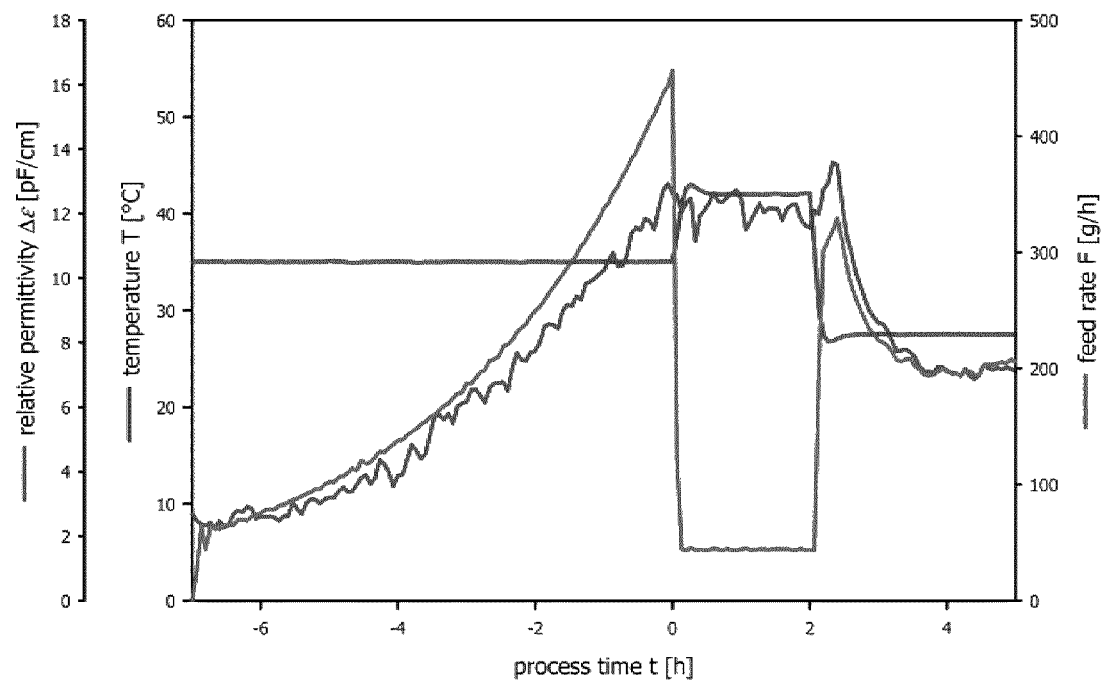

FIG. 5: Profiles of relative permittivity (green line), temperature (red line) and feed rate (blue line) during cultivation. The actual feed rate follows the capacitance signal precisely and without major delay.

Figure 6:
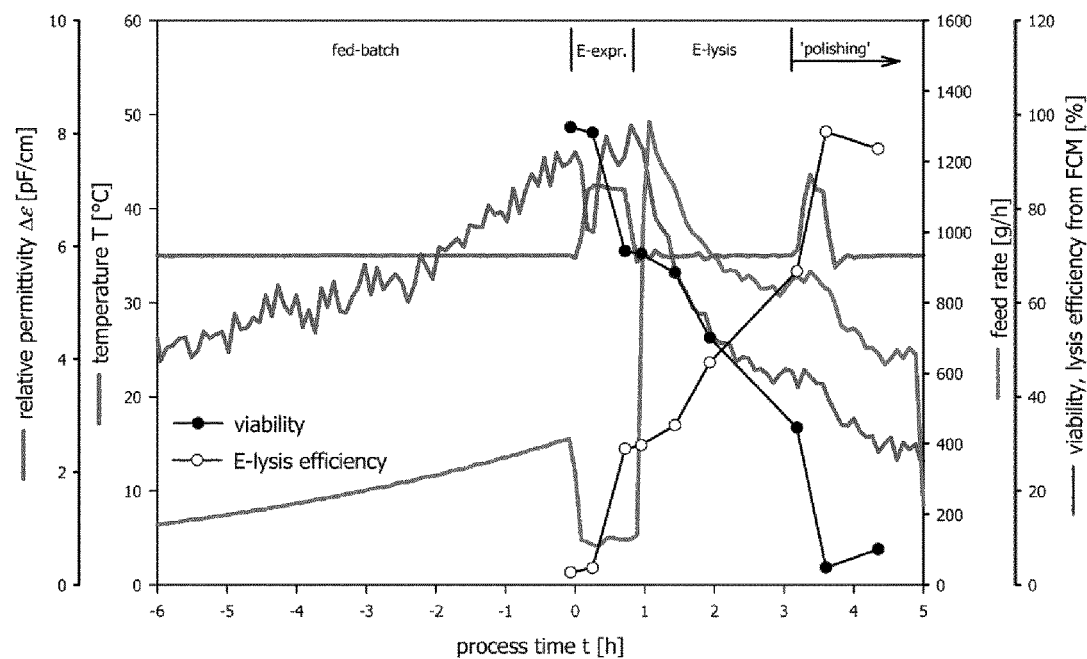

FIG. 6: Decoupled E-lysis with a "polishing step". Following E-expression and E-lysis phase (as indicated), a "polishing step" is introduced by applying a short temperature shift to 42° C.

EXAMPLES

Example 1: Materials and Methods

Bacterial Strains

*Escherichia coli* Nissle 1917 (EcN; O6:K5:H1, ΔpMut1, ΔpMut2) was provided by Ardeypharm (Herdecke, Germany). EcN carrying the temperature-inducible gene E cassette and a gentamicin resistance cassette on plasmid pGLysivb as well as the purified plasmid pGLysivb (Haidinger et al. 2001, Cytometry, 44(2):106-12) were provided by BIRD-C GmbH & CoKG (Kritzendorf, Austria). *Escherichia coli* C41 (EcC41; OverExpress™ C41 (DE3): F-ompT hsdSB (rB-mB-) gal dcm (DE3)) was purchased from Lucigene (Middleton, Wis., USA).

Both strains under investigation—EcN (pGLysivb) and EcC41 (pGLysivb)—were found to have very similar growth characteristics of $\mu_{max}$ (35° C., DeLisa medium) =0.75 h$^{-1}$ and a biomass yield coefficient $Y_{X/S}$(35° C., fed-batch)=0.5 g/g.

Preparation of CaCl$_2$/RbCl$_2$ Competent Cells (EcC41)

30 ml Luria Bertani (LB) medium were inoculated with a stock of EcC41. The culture was grown in a tempered water bath at +36° C. to an OD$_{600}$ of ~0.5. The cells were collected by centrifugation (10 min at +4° C., 1700 g), re-suspended in 20 ml pre-cooled MOPS I solution and kept on ice for 10 min. Centrifugation was repeated, the cells re-suspended in 6 ml MOPS II solution and kept on ice for 30 min. After a final centrifugation the cells were re-suspended in 480 µl MOPS II and 180 µl glycerol (50% v/v). 100 µl aliquots were stored at −80° C.

Both strains under investigation—EcN (pGLysivb) and EcC41 (pGLysivb)—were found to have very similar growth characteristics of $\mu_{max}$ (35° C., DeLisa medium)=0.75 h$^{-1}$ and a biomass yield coefficient $Y_{X/S}$ (35° C., fed-batch)=0.5 g/g.

Transformation of CaCl$_2$/RbCl$_2$ Competent Cells (EcC41)

Competent cells were thawed on ice (10 min). 2 µl plasmid-DNA (pGLysivb) was added to 100 µl of competent cells (EcC41) and kept on ice for 30 min. The cells were exposed to a heat shock at +36° C. for 2 min, transferred into 700 µl LB-medium and shaken at +36° C. for 1 h. The cells were stroke on agar plates containing selective antibiotics, positive clones were picked and incubated. A working cell bank (WCB, cryo stock of 1.8 ml) were prepared with 25% v/v glycerol and stored at −80° C.

Media

A defined medium according to DeLisa et al. supplemented with gentamycin (20 mg/l) with glucose as carbon source (batch medium glucose concentration: 20 g/l; fed-batch medium glucose concentration 400 g/l) was used.

Bioreactors

Fed-batch experiments were carried out in two stainless steel bioreactors Techfors-S with working volumes of 10 l and 20 l (Infors, Switzerland). Temperature, pH, aeration, reactor pressure and stirrer speed were controlled via the Techfors-S integrated panel. The pH was controlled at pH 7.2 using 6 M $NH_4OH$ as base and 1M $H_3PO_4$ as acid. Inlet air and oxygen were filtered by a membrane-type filter Novasip C3PFRPIA (Pall, Port Washington, N.Y.; USA). The culture vessel was sterilized in-situ at 121° C. for 20 minutes prior to inoculation.

Furthermore, a parallel quad-bioreactor system Microbiology BD (DASGIP, Jülich, Germany) with similar instrumentation was used for screening-scale experiments. The working volume of the screening-scale system is 1-2 l.

Off-gas Analysis

The off-gas concentrations of $CO_2$ and $O_2$ were quantified by a gas analyzer (Servomex, Crowborough, United Kingdom; Dr. Marino Müller A G, Egg, Switzerland) using infrared and paramagnetic principle, respectively. Air and oxygen in-flows were quantified by mass flow controllers (Vögtlin, Aesch, Switzerland).

Off-gas analysis for the DASGIP quad system was done by a GA4 (DASGIP, Jülich, Germany) module featuring BlueSens sensors for O2 and CO2 (BlueSens, Herten, Germany)

In-line Radio-frequency Impedance Measurements (RFI)

An annular type probe (Aber Instruments, Aberystwyth, Wales, UK) was applied for in-line measurements of the relative permittivity $\Delta\varepsilon$. $\Delta\varepsilon$ is estimated by using two frequencies, a high frequency accounting for non-cellular background (10 MHz) and a low frequency attributed to living bacterial cells (1 MHz). The difference between the obtained values gives the relative permittivity $\Delta\varepsilon$, which can be correlated to the viable biomass concentration. Further information on the measurement principle is given in Markx et al., 1999 Enzyme and Microbial Technology, 25(3-5), 161-171.

Culture Mode for Accumulation of Biomass (Batch/fed-batch)

A pre-culture (90/120 ml, $OD_{600}$ 1-2) was used for the inoculation of the bioreactors containing 4 and 7 l of batch medium (10/20 l working volume), respectively. At the end of the batch phase as detected by a decline in the $CO_2$ off gas concentration, an exponential fed-batch with a growth rate of $\mu=0.3$ $h^{-1}$ was started. The exponential feed rate F(t) was calculated according to Equation 2.

$$F(t) = F_0 \cdot e^{\mu \cdot t}$$

Equation 2: Calculation of the feed rate F in the exponential fed batch in g/h

The initial feed rate $F_0$ was calculated following Equation 3.

Equation 3

Calculation of the initial federate F0 for the exponential fed batch in g/h.

$$F_0 = \frac{\mu \cdot X_0 \cdot V_0 \cdot \rho_f}{S_o \cdot Y_{\frac{X}{S}}}$$

The biomass concentration at the end of the batch phase $X_0$ was estimated from the measured $OD_{600}$. The feed concentration $S_0$ is given from the medium composition, the feed density $\rho_f$ was determined gravimetrically. Cultivation parameters are summarized in Table 1.

TABLE 1

Cultivation parameters for batch/fed-batch phase

| process parameter | value |
|---|---|
| temperature [° C.] | 35 |
| pressure [bar gauge] | 1.2 |
| air flow rate [l/min] | 1 vvm |
| oxygen flow rate [l/min] | 0 to 0.1 vvm |
| stirring speed [rpm] | 900 to 1,495 |
| dissolved oxygen conc. ($dO_2$) | >20% |
| pH | 7.2 ± 0.01 |

Scale-down Model

For screening-scale experiments scale-down model was used to ensure that the culture would stay a certain minimal number of generation times (in this case: 2) in fed-batch mode without reaching high cell densities. The glucose concentration in the batch phase was decreased to 8 g/l and the fed-batch phase was conducted with a reduced glucose concentration $S_0=100$ g/l in the feed. Table 2 shows a comparison between the fed-batch processes as conducted in pilot-scale fermentation vs. the scale-down model.

TABLE 2

Summary of the applied downscale model based on the generation time

| process parameter | pilot scale 20 l | scale-down model |
|---|---|---|
| specific growth rate (fed-batch) | 0.3 h−1 | 0.3 h−1 |
| initial glucose concentration (batch) | 20 g/l | 10 g/l |
| generation times (fed-batch) | 2 | 2 |
| glucose concentration (feed) | 400 g/l | 100 g/l |
| time (fed-batch) | 6.6 h | 6.6 h |

Process Management

The process information management system (PIMS) Lucullus (SecureCell AG, Schlieren Switzerland) was used for monitoring and control of the bioprocesses. Tools for volume estimation and soft sensing (see above) were implemented in Lucullus-integrated interface tool Sim-Fit. The $q_S$ control strategy during E-lysis phase was implemented using simple calculator devices as outlined later in this description.

Cumulated Soft-Sensor for Biomass Estimation

A cumulated soft-sensor as described in Wechselberger et al (see above) was used for the estimation of the biomass concentration. In short, the applied soft sensor is based on a redundant equation system (redundancy of 1) involving the degree of reduction as well as the carbon balance in matrix formulation. The substrate uptake rate ($r_S$) is calculated via the measured feed flow F(t) and the known feed concentration $S_0$ and density $\rho_f$. Carbon dioxide evolution ($r_{CO2}$) and oxygen uptake rates ($r_{O2}$) are calculated from the measured air and oxygen flow rates as well as the measured oxygen and carbon dioxide concentration in the off-gas.

The over-determined equation system allows the estimation of the biomass formation rate rx assuming a fixed C-molar stoichiometry of the cell population ($CH_{1.8}N_{0.23}O_{0.56}$, ash content 5.5%). The biomass formation rate rx is integrated and cumulated to sense the total biomass formed. Division through the current broth volume V(t) gives the biomass concentration. The soft-sensor is started simultaneously with the exponential feed ramp of the fed-batch. The estimated biomass concentration at the end of the batch phase is used as a starting value for the soft sensor.

At-line and Off-line Analytics

Biomass

Biomass concentrations were quantified gravimetrically after drying for a minimum of 72 h at 105° C. Samples were centrifuged (5,000 rpm, 10 min) and the pellet was washed with distilled water. Biomass concentrations for the start of the fed-batch (Equation 2) as well as for initial values of the soft-sensor (see above) were estimated by photometric principle ($DCW=0.33*OD_{600}$).

Substrate and Small Metabolites

Lysis phase glucose as well as acetate concentrations of the supernatant were quantified via HPLC (using the HPLC column Supelcogel C-610, Sigma Aldrich, flow rate: 0.5 ml/min, eluent: 0.1% $H_3PO_4$/NaN3, 30° C., Refractive Index (RI) detector). Prior to analysis, samples were diluted (1:5) to allow filtration through a 0.2 μm filter.

Flow Cytometry (FCM) Measurements

For FCM, a Cube 6 system (Partec, Monster, Germany) with a 488 nm blue solid state laser was used. Samples are diluted appropriately and stained with two fluorescent dyes: RH 414 (abs./em.: 532/718 nm, final conc.: 3 nM) for staining cell membranes and DiBAC4(3) (abs./em.: 493/516 nm, final conc.: 0.75 nM) for determining cell viability (both dyes: AnaSpec, Fremont Calif., USA). RH 414 signals were picked up in channel FL2 (orange) defining a gate for exclusion of non-cellular background. Combination of FSC (forward scatter) and FL1 (green) signals were used to identify regional gates for living cells (R1), dead but intact cells (R2) and bacterial ghosts (R3). The lysis efficiency (LE) can be calculated directly from the particle counts in the respective regions:

Equation 4

Calculating the lysis efficiency LE from cell counts in the regions R1-3.

$$LE = \frac{R3}{(R1+R2+R3)} \cdot 100\%$$

Western Blot for Protein E Detection

Transfer of proteins to precast gels was done by wet blot using an XCell II™ Blot Module (Invitrogen, Carlsbad, Calif., USA). The protein transfer was verified by staining with PonceauS. Blocking was done for 1 h at room temperature using Roti®-Block (Roth, Karisruhe, Germany) working solution.

Antibody incubation and development: membranes were washed for 5 min in TBST buffer and then incubated with the primary antibody for 2 hours at room temperature. After incubation membranes were washed 4×5 min in TBST. Then the secondary antibody (HRP-coupled) was applied for 1 h and the membranes were washed 4×5 min in TBST. The membranes were incubated with 5 ml SuperSignal West Pico Chemiluminescent Substrate (Thermo Fisher Scientific, Rockford, Mass., USA) for 3 min. All steps were performed under agitation. Detection was done with ChemiDoc™ XRS (Bio-Rad, Hempstead, UK) using the software QuantityOne (Bio-Rad, Hempstead, UK).

Example 2: Radio Frequency Impedance Measurement for Process Monitoring and Control Radio frequency impedance measurement (RFI) has emerged as a valuable process analytical tool for the monitoring and control of mammalian, yeast and microbial processes (Carvell et al., 2006 Cytotechnology, 50(1-3), 35-48, Soley et al., 2005 J. Biotechnol., 118(4), 398-405, Yardley et al., Biotechnol. Genet. Eng. Rev. 17, 3-35). The (bio-) physical background of RFI is reviewed in Asami et al., 2002 Journal of Non-Crystalline Solids, 305(1-3), 268-277, Davey et al., 1993 Analytica Chimica Acta, 279, 155-161).

Control strategies on the basis of RFI for cell culture processes included the feed-back control of living cell specific perfusion rates, the estimation of metabolic activity and control of the glutamine feed rate in mammalian cell culture. Furthermore, RFI was used for the calculations of specific heat flow rate in cell culture processes which can be utilized as a possible control variable. For microbial systems, applications of RFI typically focus on on-line monitoring of viable biomass. Successful integration of RFI as a representative measure of viable cell concentration in control strategies for production of heterologous proteins in *E. coli* are reported in Kaiser et al., 2008 Eng. Life Sci., 8(2), 132-138. Furthermore, applications for process control on the basis of physiological information obtained by RFI were suggested in Matanguihan et al., 1994 Bioprocess. Eng., 11(6), 213-222.

Example 3: First Principle Soft-sensing for Biomass Estimation

The term "soft-sensor" or "software sensor" refers to mathematical software that calculates non- or difficultly accessible process variables from easily accessible process data using a suitable process model. A review on the performance of soft-sensors for the applications on bioprocesses is given by de Assis et al., 2000 Chemical Engineering, 24(2-7), 1099-1103. The biomass dry cell weight concentration (as catalyst or product) can be considered a key variable for the basis of bioprocess control and monitoring approaches. Hence, the real-time accessibility of this process variable is of great interest. Next to different hard-type sensor following different measurement principles soft-sensors can be applied to make this variable accessible in real-time. Soft-sensors for biomass estimation can be roughly categorized in soft-sensors in need of training data sets, e.g. on the basis of artificial neural networks, and fist-principle soft sensors, e.g. on the basis of elemental balancing. Fist-principle soft sensor following a cumulated elemental balancing approach involving a redundant equation system constrained by carbon (C—) and degree of reduction (DoR-) balances for the estimation of biomass as described in Sagmeister et al., 2013 Chemical Engineering Science, 96, 190-198 and Wechselberger et al, 2012 Engineering, 36(9), 1205-1218 has been included in a newly developed PAT strategy for dynamic bioprocess control.

Example 4: Induction of Gene E Expression by a Temperature Pulse

Based on prior knowledge that for a single cell E-lysis is inexorable within one minute after effective induction of gene E and that less than 1,000 molecules of protein E per cell are required for successful E-lysis, it was suggested that decoupling can be accomplished by a short temperature pulse of 10 min at 42° C. Accumulation of a biomass X=40 g/l DCW through an exponential fed-batch with a specific substrate uptake rate of $q_S$=0.6 g/gh (i.e. µ=0.3 h$^{-1}$) using EcN (pGLysivb) was followed by a temperature pulse (10 minutes at 42° C.) for inducing gene E expression. As expected, no immediate sign of E-lysis onset was observed within this 10 min timeframe as reflected by RFI measurements (green line, FIG. 2). Subsequently, the temperature was reduced to 27.5° C. Within the following 2 hours of the process the relative permittivity was observed to decrease simultaneously with the decline of cell viability (FCM data, full spheres, FIG. 2). As the loss of viability was accompanied by a commensurate appearance of BGs (FCM data, empty spheres, FIG. 2) it could be proven that the permittivity signal indeed reflects the actual progress of E-lysis. No foaming was observed during E-lysis phase.

The process using only a short temperature pulse yielded a final lysis efficiency of 85%.

Example 5: Demonstration of the Decoupled E-lysis Process

The decoupled E-lysis process was demonstrated at 2 l scale with EcC41 (pGLysivb) as depicted in FIG. 3 (A). Biomass was accumulated in an exponential fed-batch with a specific substrate uptake rate of $q_S$=0.6 g/gh (µ=0.3 h$^{-1}$). Subsequently, the specific substrate uptake rate was reduced to 0.1 g/gh via reduction of the feed rate. Following the reduction of $q_S$, the temperature was increased to 42° C. for expression of gene E. FCM measurements verified that population was not immediately affected by E-lysis as the viability decreases only slightly during the E-expression phase (whole spheres, FIG. 3 (A)). After 1 h of gene E expression the temperature was reduced to 27.5° C. where the temperature-inducible promoter is tightly closed and gene E can no longer be expressed. Simultaneously, the specific substrate uptake rate was shifted back to $q_S$=0.6 g/gh. Following this up-shift in $q_S$ the E-lysis efficiency as detected by FCM increased to 76% (empty spheres, FIG. 3 (A)).

The described process was successfully carried out using the strains EcC41 (as shown) as well as EcN (data not shown). Overall it can be concluded that the specific substrate uptake rate $q_S$ (a measure for the cell specific metabolic activity) strongly has a strong impact on the lysis competence of the cells. The process can be held in a non-lysis-competent physiological state by means of a reduction of the specific substrate uptake rate even though protein E is present (protein E found in bacterial pellet through Western Blot analysis, data not shown). Subsequently, E-lysis can be triggered by a change in $q_S$ which means that the impact on the physiological state through $q_S$ is reversible. These findings consolidate the basis for the suggested decoupled process mode.

Determination of the Minimal $q_S$ Value Necessary to Trigger E-lysis

EcC41 (pGLysivb) was grown at 20 l scale to a biomass concentration of X=30 g/l in an exponential fed-batch ($q_S$=0.6 g/gh, T=35° C.). Gene E-expression was induced by a temperature shift to 42° C. while $q_S$ was reduced to 0.1 g/gh in order to prevent effective E-lysis. The RFI signal remained constant during E-expression phase indicating that E-lysis was successfully (green line, FIG. 3 (B)). After 1 h of E-expression the temperature was reduced to 27.5° C. and a soft-sensor-assisted $q_S$-controller was started. The specific substrate uptake rate was gradually increased over a time frame of 2 h. Approximately 1 h hour into the E-lysis phase the RFI signal dropped abruptly (vertical arrow, FIG. 3 (B)) indicating the onset of E-lysis. Thus, we have found that $q_S$ is the sole trigger for E-lysis (where $q_{S,min}$ is a function of temperature, data not shown) and the threshold value for lysis onset at 27.5° C. is $q_{S,min}$=0.4 g/gh; as indicated by the horizontal arrow in FIG. 3 (B). With this data the feasibility of decoupling E-expression and E-lysis by means of $q_S$ was shown.

Example 6: Control of the Specific Substrate Uptake Rate in the Lysis Phase

As the specific substrate uptake rate $q_S$ could be identified as major critical process parameter (CPP) for the described BG production with decoupled E-expression and E-lysis, a $q_S$-based control strategy was developed for optimization purposes.

The relative permittivity signal was found to correlate with the decrease of living cell counts in the E-lysis phase as obtained from FCM (see example 4). As during E-lysis the bacteria lose their membrane potential, it can be assumed that the RFI signal accurately reflects the remaining fraction of viable cells in the population, as reviewed in Yardley et al., 2000 Biotechnol. Genet. Eng. Rev. 17, 3-35. Since this signal is available in real time with a high timely resolution, it was chosen for the development of a $q_S$-based control strategy with the goal of ensuring a constant substrate uptake rate during the course of the highly dynamic E-lysis process.

In analogy with Equation 4 the feed rate set point for a desired specific substrate uptake rate $q_{S,SP}$ at any given time can be calculated as given in Equation 5.

Equation 5

Calculation of the feed rate set point as a function of a desired specific substrate uptake rate $q_{S,SP}$ at variable times $$F(t) = \frac{q_{S,SP} \cdot X(t) \cdot V(t) \cdot \rho_f}{S_0}$$

The current values for the viable biomass X(t) and broth volume V(t) are thereby unknown. The broth volume could be calculated in real-time using the initial reactor volume and the known in-fluxes of feed, base and gasses as well as the exhaust gas concentrations of $O_2$ and $CO_2$. The concentration of viable biomass during E-lysis phase can be calculated from the RFI signal. During fed-batch the viable biomass concentration was estimated by a first-principle soft-sensor and at the end of the fed-batch phase a linear correlation between the viable biomass X and the relative permittivity Δε was established at-line according to Equation 6.

$$X(t) = m_\varepsilon \cdot \Delta\varepsilon + b_\varepsilon$$

Equation 6: Calculation of the viable biomass concentration X(t) as a function of the permittivity Δε, $m_\varepsilon$ and $b_\varepsilon$ are correlation constants for the linear equation.

Since the change in viable biomass concentration during E-lysis is highly dynamic the feed rate was controlled directly via the feed pump set-point. As described for the biomass calculation a linear correlation between feed rate F(t) and the feed pump set point $P_{SP}(t)$ was done at-line according to Equation 7.

$$P_{SP}(t) = m_P \times F(t) + b_P$$

Equation 7: Calculation of the pump rate set-point PSP(t) as a function of the flow rate F(t), $m_P$ and $b_P$ are correlation constants for the linear equation.

Tracking of process inputs and all described computations (soft-sensing, volume calculation, calculation of feed rate set points, conversion of permittivity to biomass and feed rate set point to pump set point) were done through the PIMS. The correlation constants for the linear equations were implemented shortly before the E-lysis phase began. FIG. 4 shows a schematic view of the described PAT-strategy for controlling $q_S$ during E-lysis phase. The strategy was successfully implemented with respect to controlling $q_S$ on the basis on RFI (see FIG. 5).

Example 7: Using a "Polishing Step" for Increasing E-lysis Efficiency

In order to push E-lysis efficiencies towards the desired range, we performed a "polishing step". Based on the assumption that the low overall E-lysis efficiencies could be explained by insufficient induction of gene E expression in a section of the bacterial population, a temperature pulse was applied at the end of the E-lysis phase. This temperature pulse was implemented without reducing the feed rate (as described in Example 4).

In a feasibility experiment with EcC41 (pGLysivb) a fed-batch (35° C., $q_S$=0.3 g/gh) was conducted in 20 l scale for biomass accumulation of 36 g/l. The E-expression phase was conducted for 1 h at 42° C. with $q_S$ (E-expr.)=0.1 g/gh. Feeding during E-lysis phase was controlled using the strategy as described above (Example 6) with $q_S$ (E-lysis)=1.0 g/gh at T (E-lysis)=35° C. After 2 h of E-lysis phase a temperature shift to 42° C. was implemented as "polishing step". Cell viability and E-lysis efficiency was evaluated from FCM data (FIG. 6).

During E-lysis phase the E-lysis efficiency was only 60%, however, once the temperature-shift was implemented the E-lysis efficiency increased rapidly to a maximal value of 96%. With this experiment, we could show that E-lysis efficiencies of the desired magnitude are possible with the principle of decoupling E-expression and E-lysis phase. Since foaming was no issue with both the $q_S$-controlled decoupled E-lysis concept and the method using a temperature pulse, the combination of both, i.e. decoupled E-lysis with a "polishing step", is suitable for a high-density bacterial ghost production process.

CONCLUSION

Protein E mediated lysis at elevated biomass densities (50 g DCW/l) and elevated temperatures is accompanied by excessive foaming. Hence, conventional fed-batch production processes involving the heat inducible $\lambda p_R$-cI857 promoter system are not very suitable.

Decoupling of a lytic gene expression and actual protein mediated lysis is feasible using process technological parameters. The specific substrate uptake rate ($q_S$) was identified as a critical parameter to control the lysis process of the bacterial cells.

A fed-batch process method decoupling lytic gene expression and actual lysis of the bacterial cells by means of the specific substrate rate ($q_S$) was developed to overcome the previously observed foaming issues.

The relative permittivity signal (RFI) correlates linearly with the living cell count, allowing the observation of the lysis process in real-time.

On the basis of the RFI signal, a strategy was implemented providing control of the specific substrate uptake rate $q_S$ within the lysis phase. Using a first principle soft-sensor, the necessary calibration between relative permitivity and viable biomass can be done at-line without prior strain-specific information.

Temperature pulses (42° C.) of 10 minutes are sufficient to trigger protein E mediated lysis, even if the temperature is reduced to 20° C. thereafter to avoid foaming with E-lysis efficiencies of about 85%.

A multivariate study was performed trying to identify the critical process parameters for the decoupled lytic gene expression/lysis process, identifying $q_S$ during the lytic gene expression phase. The optimum value for $q_S$ that allows lytic gene expression decoupled from the lysis process was found at 0.1 g/gh.

Combining the $q_S$-controlled decoupled lysis and a second temperature pulse (42° C.) as a "polishing step", an lysis efficiency of 96% was obtained in a feasibility run showing that the desired product specifications, e.g. a high lysis efficiency can be reached.

The invention claimed is:
1. A method for producing a bacterial ghost preparation comprising the steps:
    (a) providing bacterial cells comprising a lytic gene encoding a protein capable of forming a tunnel structure in the bacterial cell envelope wherein the expression of the lytic gene is under operative control of a regulatable promoter,
    (b) cultivating the bacterial cells under conditions wherein the lytic gene is not expressed to a final biomass concentration of about 10-80 g dry cell weight (DCW)/L,
    (c) after step (b), subjecting the bacterial cells to conditions wherein the lytic gene is expressed by inducing the regulatable promoter but lysis of the bacterial cells is repressed and wherein the bacterial cells are subjected to an at least substantially stationary state,
    (d) after step (c), subjecting the bacterial cells to conditions wherein lysis of the bacterial cells takes place, and thereafter carrying out a further promoter induction step by inducing the regulatable promoter, and
    (e) obtaining the resulting bacterial ghosts.
2. The method according to claim 1, wherein the bacterial cells are Gram-negative bacterial cells.
3. The method according to claim 1, wherein the lytic gene encoding the lytic protein is the bacteriophage (Φ)X174 lytic gene E.
4. The method according to claim 1, wherein the regulatable promoter is a chemically or thermally regulatable promoter.
5. The method according to claim 4, wherein the chemically regulatable promoter is a lac or trp promoter.
6. The method according claim 4, wherein the thermally regulatable promoter is a λcI857 promoter.
7. The method according to claim 1, wherein the cultivation of bacterial cells is carried out as a fed-batch cultivation.
8. The method according to claim 1, wherein the cultivation of the bacterial cells is carried out to a final biomass concentration of about 20 -70 g DCW/L culture medium.
9. The method according to claim 1, wherein step (b) comprises cultivating the bacterial cells at a specific substrate uptake rate $q_s$ of at least about 0.4 g/gh (amount of substrate consumed per time in g/gh).
10. The method according to claim 1, wherein in step (c) the specific substrate uptake rate $q_s$ is about 0.1-0.3 g/gh.
11. The method according to claim 1, wherein step (c) comprises inducing the regulatable promoter by adding an inducing chemical compound and/or by adjusting the temperature to an expression permissive temperature.

12. The method according to claim 1, wherein in step (d) the lysis of the bacterial cells is induced by providing a growth impulse.

13. The method according to claim 1, wherein in step (d), after subjecting the bacterial cells to lytic conditions, the additional promoter induction step is a chemically or a thermally promoter induction step.

14. The method according to claim 1, wherein residual non-lysed bacterial cells are inactivated.

15. The method according to claim 14, wherein inactivation of residual non-lysed bacterial cells comprises inactivating with a chemical inactivator capable of destroying the residual non-lysed bacterial cells.

16. The method according to claim 14, wherein inactivation of residual non-lysed bacterial cells comprises co-expressing a nuclease.

17. The method according to claim 1, wherein a E-lysis efficiency of at least about 70% is reached.

18. The method according to claim 1, wherein the culture medium conditions are monitored at least during step (c) and step (d).

19. A method for recombinantly producing a protein of interest comprising the steps:
(a) providing bacterial cells comprising (i) a lytic gene encoding a protein capable of forming a tunnel structure in the bacterial cell envelope wherein the expression of the lytic gene is under operative control of a regulatable promoter and (ii) a gene encoding a protein of interest,
(b) cultivating the bacterial cells under conditions wherein the lytic gene is not expressed to a final biomass concentration of about 10-80 g dry cell weight (DCW)/L,
(c) after step (b), subjecting the bacterial cells to conditions wherein the lytic gene is expressed by inducing the regulatable promoter but lysis of the bacterial cells is repressed and wherein the bacterial cells are subjected to an at least substantially stationary state,
(d) after step (c), subjecting the bacterial cells to conditions wherein lysis of the bacterial cells takes place, and thereafter carrying out a further promoter induction step by inducing the regulatable promoter, and
(e) recovering and optionally purifying the protein of interest, which has been expressed during step (b) and/or step (c).

20. A method for recombinantly producing bacteriophage (Φ)X174 protein E or derivatives thereof comprising the steps:
(a) providing bacterial cells comprising a lytic gene encoding the lytic protein E or derivatives thereof wherein the expression of the lytic gene is under operative control of a regulatable promoter,
(b) cultivating the bacterial cells under conditions wherein the lytic gene is not expressed to a final biomass concentration of about 10-80 g dry cell weight (DCW)/L,
(c) after step (b), subjecting the bacterial cells to stationary state conditions wherein the lytic gene is expressed by inducing the regulatable promoter but lysis of the bacterial cells is repressed,
(d) after step (c), subjecting the bacterial cells to conditions wherein lysis of the bacterial cells takes place, and thereafter carrying out a further promoter induction step by inducing the requlatable promoter, and
(e) recovering and optionally purifying the protein E or derivatives thereof.

21. The method according to claim 2, wherein the Gram-negative bacterial cells are *E. coli* cells.

22. The method according to claim 8, wherein the cultivation of the bacterial cells is carried out to a final biomass concentration of about 30-60 g DCW/L culture medium.

23. The method according to claim 22, wherein the cultivation of the bacterial cells is carried out to a final biomass concentration of about 40-50 g DCW/L culture medium.

24. The method according to claim 12, wherein the growth impulse comprises providing nutrients to the culture medium.

25. The method according to claim 24, wherein the growth impulse comprises providing nutrients to the culture medium to obtain a substrate uptake rate $q_s$ of at least about 0.4 g/gh.

26. The method according to claim 15, wherein said chemical inactivator is betapropiolactone.

27. The method according to claim 16, wherein said nuclease is an S-nuclease.

28. The method according to claim 17, wherein a E-lysis efficiency of at least about 80% is reached.

29. The method according to claim 28, wherein a E-lysis efficiency of at least about 90% is reached.

30. The method according to claim 29, wherein a E-lysis efficiency of at least about 96% is reached.

31. The method according to claim 18, wherein the culture medium conditions are monitored by radio frequency impedance measurement.

* * * * *